(12) United States Patent
Jeong

(10) Patent No.: US 9,326,921 B1
(45) Date of Patent: May 3, 2016

(54) FUNCTIONAL SOAP

(71) Applicant: NANOPOLY CO., LTD., Seoul (KR)

(72) Inventor: Gu Wan Jeong, Seoul (KR)

(73) Assignee: NANOPOLY CO., LTD., Seoul (KR)

( * ) Notice: Subject to any disclaimer, the term of this patent is extended or adjusted under 35 U.S.C. 154(b) by 0 days.

(21) Appl. No.: 14/637,338

(22) Filed: Mar. 3, 2015

(51) Int. Cl.
| | |
|---|---|
| *A61K 8/19* | (2006.01) |
| *A61K 8/92* | (2006.01) |
| *A61K 8/97* | (2006.01) |
| *A61Q 19/10* | (2006.01) |

(52) U.S. Cl.
CPC . *A61K 8/19* (2013.01); *A61K 8/922* (2013.01); *A61K 8/97* (2013.01); *A61Q 19/10* (2013.01); *A61K 2800/413* (2013.01); *A61K 2800/651* (2013.01); *A61K 2800/652* (2013.01)

(58) Field of Classification Search
None
See application file for complete search history.

(56) References Cited

U.S. PATENT DOCUMENTS

| | | | | |
|---|---|---|---|---|
| 7,989,599 | B2 * | 8/2011 | Suzuki | A23L 1/30 435/74 |
| 9,155,310 | B2 * | 10/2015 | Agrawal | C09D 5/14 |
| 9,161,544 | B2 * | 10/2015 | Agrawal | C09D 5/14 |

FOREIGN PATENT DOCUMENTS

| | | |
|---|---|---|
| KR | 20080108714 | 12/2008 |
| KR | 20100019652 | 2/2010 |

* cited by examiner

*Primary Examiner* — Necholus Ogden, Jr.
(74) *Attorney, Agent, or Firm* — IPLA P.A.; James E. Bame

(57) ABSTRACT

A functional soap includes nanoscale platinum, gold, silver, organic germanium and organic selenium to prepare soap, wherein anti-bacterial, sterilizing, skin irritation relieving and skin moisturizing functions provided in platinum, gold, silver, organic germanium, and organic selenium are added to the washing effect of the conventional soap.

1 Claim, 5 Drawing Sheets

TEM Image of Nano Platinum (Average particle Size: 30nm

FUNCTIONAL SOAP

BACKGROUND

The present invention relates to a functional soap, and more specifically to a soap having anti-bacterial, sterilizing, skin irritation relieving, and skin moisturizing functions.

In general, soaps are used to remove fats of a skin and waste products of the skin.

Conventional soaps are made using animal oil or vegetable oil as a main raw material of soap base.

The conventional soap removes fats and waste products from the skin, but does not have anti-bacterial, sterilizing and skin irritation relieving functions for trouble generated in the skin and germs existing in the skin. In addition, if the skin is scratched because the skin is dry or itchy or has atopic skin disease symptoms, the skin becomes coarser and may be exposed to germs. In this regard, when using a general cleaning soap, it is rarely to help for treating or alleviating skin diseases. Accordingly, a functional soap capable of preventing or alleviating bacterial secondary infection caused by such a skin disease is required in the art. The present inventor has been trying to find a new functional soap based on the requirement, and as a result, completes the present invention which relates to a technique of manufacturing a functional soap containing nanoscale granular effective ingredients.

SUMMARY OF THE INVENTION

In consideration of the above—mentioned circumstances, it is an object of the present invention to provide a functional soap which contains nanoscale granular effective ingredients having anti-bacterial, sterilizing, skin irritation relieving, and skin moisturizing functions, so as to use for protecting the skin from various types of germs when washing the face or body.

In order to accomplish the above-described object, there is provided a soap which contains a raw material of a soap base, and nanoscale platinum, gold, silver, organic germanium and organic selenium mixed in the raw material, in which the platinum has a purity of 99.9% and a particle size of 1-50 nm, and is mixed in an amount of 0.2-10 ppm, the gold has a purity of 99.9%, a particle size of 1-9 nm, and is mixed in an amount of 0.5-20 ppm, the silver has a purity of 99.9%, a particle size of 1-9 nm, and is mixed in an amount of 0.5-20 ppm, the organic germanium has a purity of 99.9%, a particle size of 5-50 nm, and is mixed in an amount of 0.1-10 ppm, and the organic selenium has a purity of 99.9%, a particle size of 1-20 nm, and is mixed in an amount of 0.1-10 ppm, wherein the raw material may include coconut kernel and oil ingredient as main ingredients, the platinum, gold, silver, organic germanium and organic selenium may be mixed in the main raw material of soap base in nanoparticles, and the nanoparticles mixed in the raw material may include jojoba Seed Oil, Aloe Barbadensis Leaf Extract, Chamomile Oil, Tocopherol, Phytosqualane and Grape Seed Oil ingredients which are mixed therein as supplemental agents.

According to the present invention, since the functional soap contains nanoparticles of platinum, gold, silver, organic selenium and organic germanium, it is possible to provide anti-bacterial, sterilizing, skin irritation relieving, and skin moisturizing effects when washing the face or body by using the soap.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

Hereinafter, embodiments according to the present invention will be described. However, those skilled in the art will appreciate that such embodiments are provided for illustrative purposes and do not limit subject matters to be protected as disclosed in the detailed description and appended claims. Therefore, it will be apparent to those skilled in the art that various alterations and modifications of the embodiments are possible within the scope and spirit of the present invention.

A functional soap according to the present invention includes coconut kernel and oil ingredients which are used as a main raw material of soap base and nanoparticles mixed therein, and jojoba Seed Oil and Grape Seed Oil which are auxiliary ingredients of soap generally used in the art, and mixed as supplemental agent therein. The functional soap of the present invention includes a raw material which is generally used in a vegetable soap, and nanoscale platinum, gold, silver, organic germanium and organic selenium added thereto.

Figure 1:
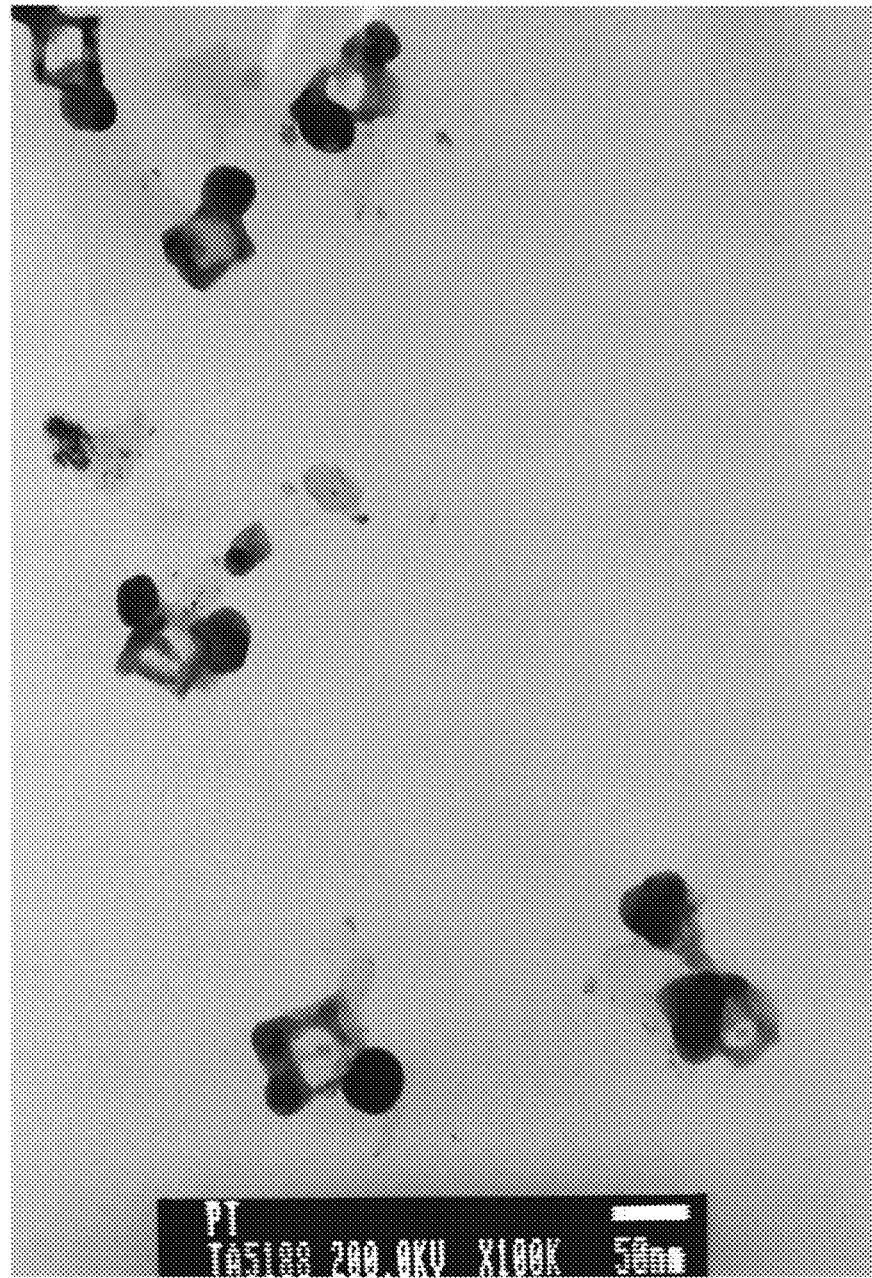
FIG. 1 is a transmission electron microscope (TEM) photograph of nano platinum particles.

FIG. 1 is a transmission electron microscope (TEM) photograph of nano platinum particles.

The platinum used in the present invention has a purity of 99.9% and a particle size of 1-50 nm, and is mixed in an amount of 0.2-10 ppm in the soap raw material. Platinum has anti-bacterial, sterilizing and smell removing effects.

Figure 2:
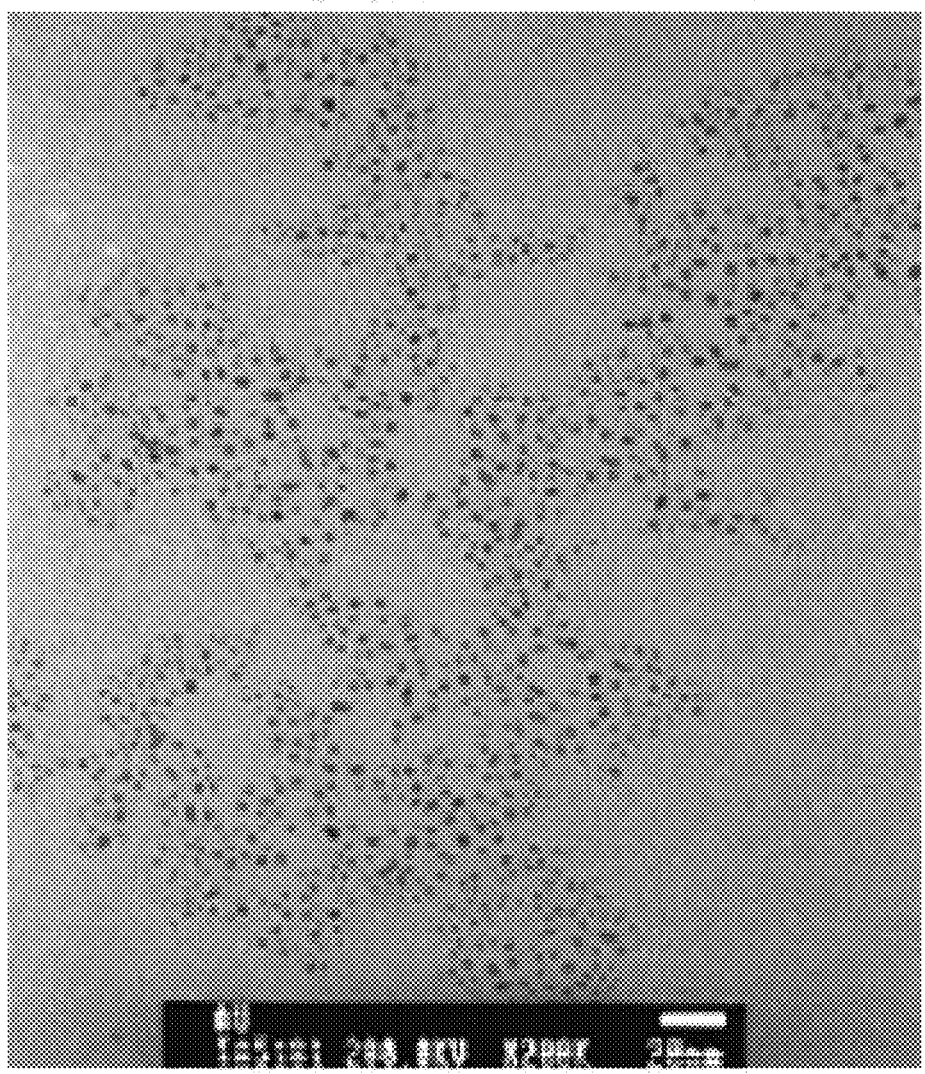
FIG. 2 is a transmission electron microscope (TEM) photograph of nano gold particles.

FIG. 2 is a transmission electron microscope (TEM) photograph of nano gold particles.

The gold used in the present invention has a purity of 99.9% and a particle size of 1-9 nm, and is mixed in an amount of 0.5-20 ppm in the soap raw material. Gold is known to have anti-bacterial, sterilizing and stabilization effects.

Figure 3:
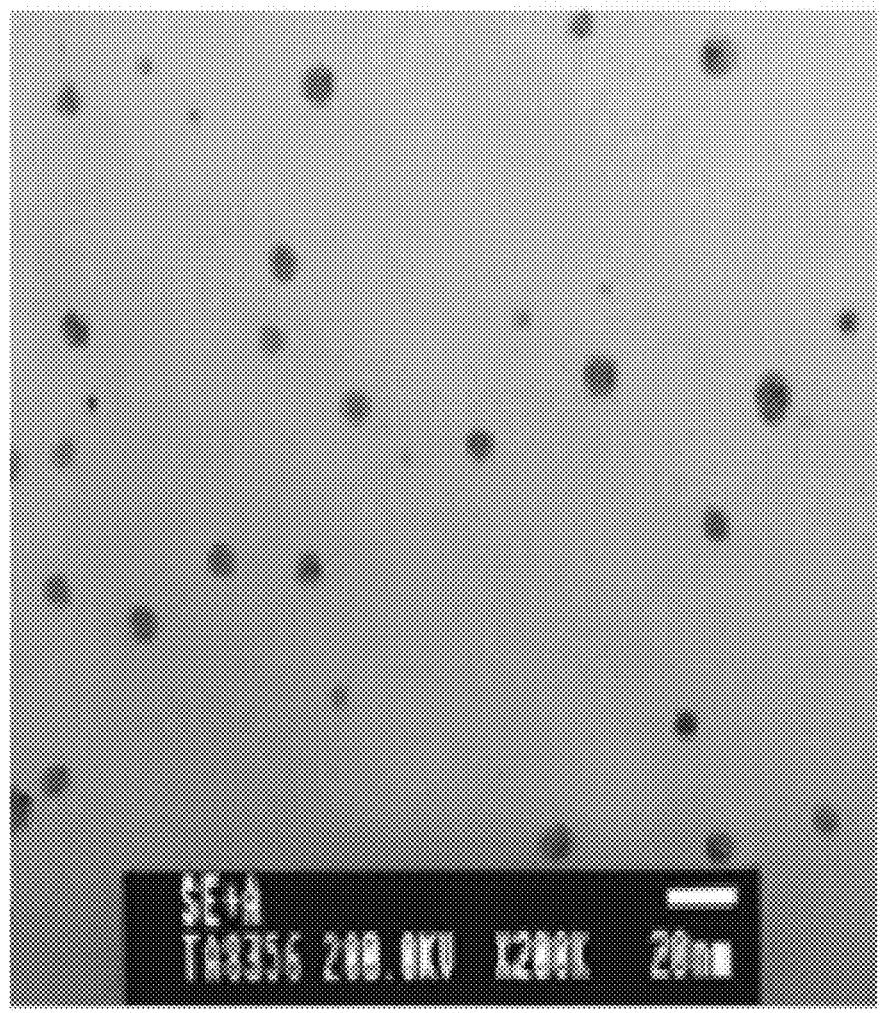
FIG. 3 is a transmission electron microscope (TEM) photograph of nano silver particles.

FIG. 3 is a transmission electron microscope (TEM) photograph of nano silver particles.

The silver used in the present invention has a purity of 99.9% and a particle size of 1-9 nm, and is mixed in an amount of 0.5-20 ppm in the soap raw material. Silver has sterilizing, anti-bacterial and anti-fungal effects. Silver is harmless to human body, has an outstanding sterilization effect, and is well known as a natural antibiotic without tolerance.

Figure 4:
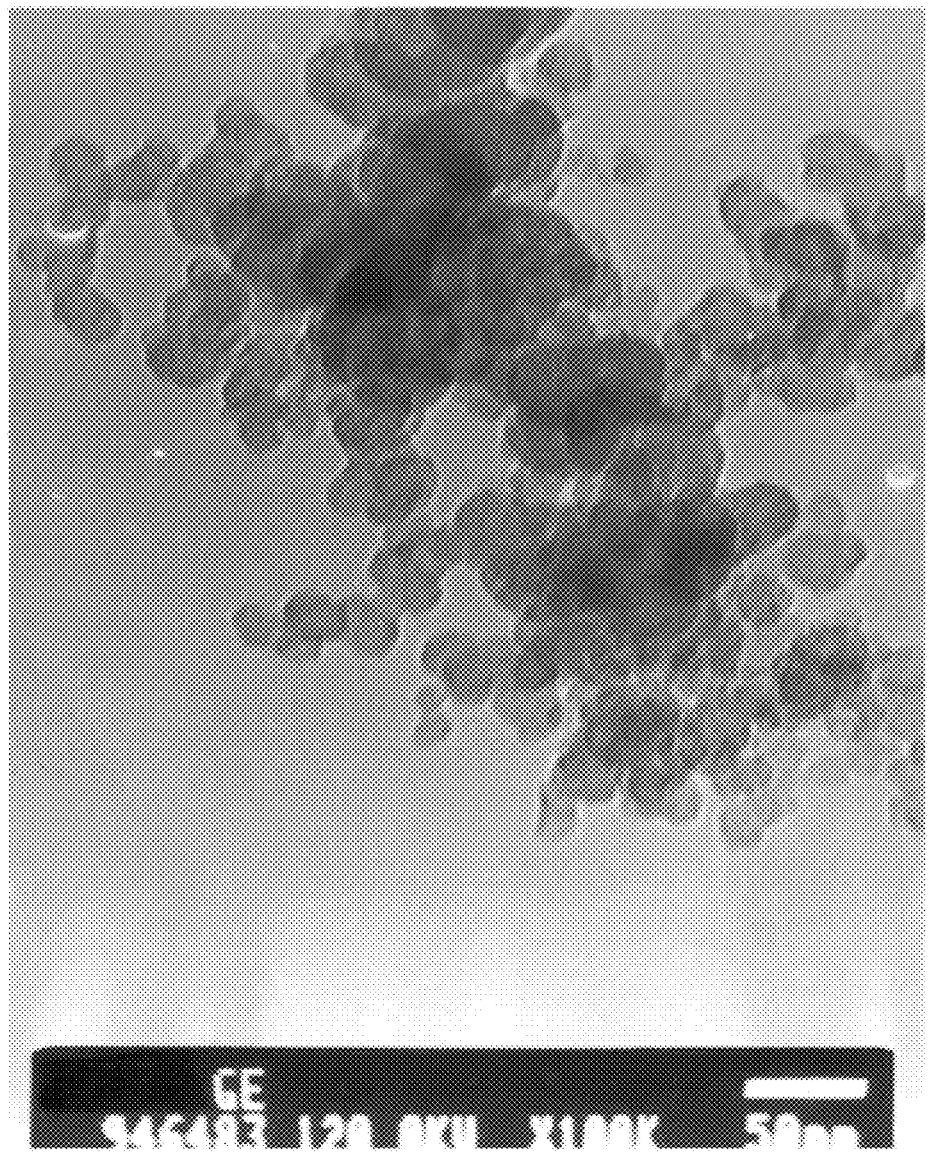
FIG. 4 is a transmission electron microscope (TEM) photograph of nano organic germanium particles.

FIG. 4 is a transmission electron microscope (TEM) photograph of nano organic germanium particles.

The organic germanium used in the present invention has a purity of 99.9% and a particle size of 5-50 nm, and is mixed in an amount of 0.1-10 ppm in the soap raw material. Organic germanium is known to have skin moisturing, anti-aging and immunity-improving functions.

Figure 5:
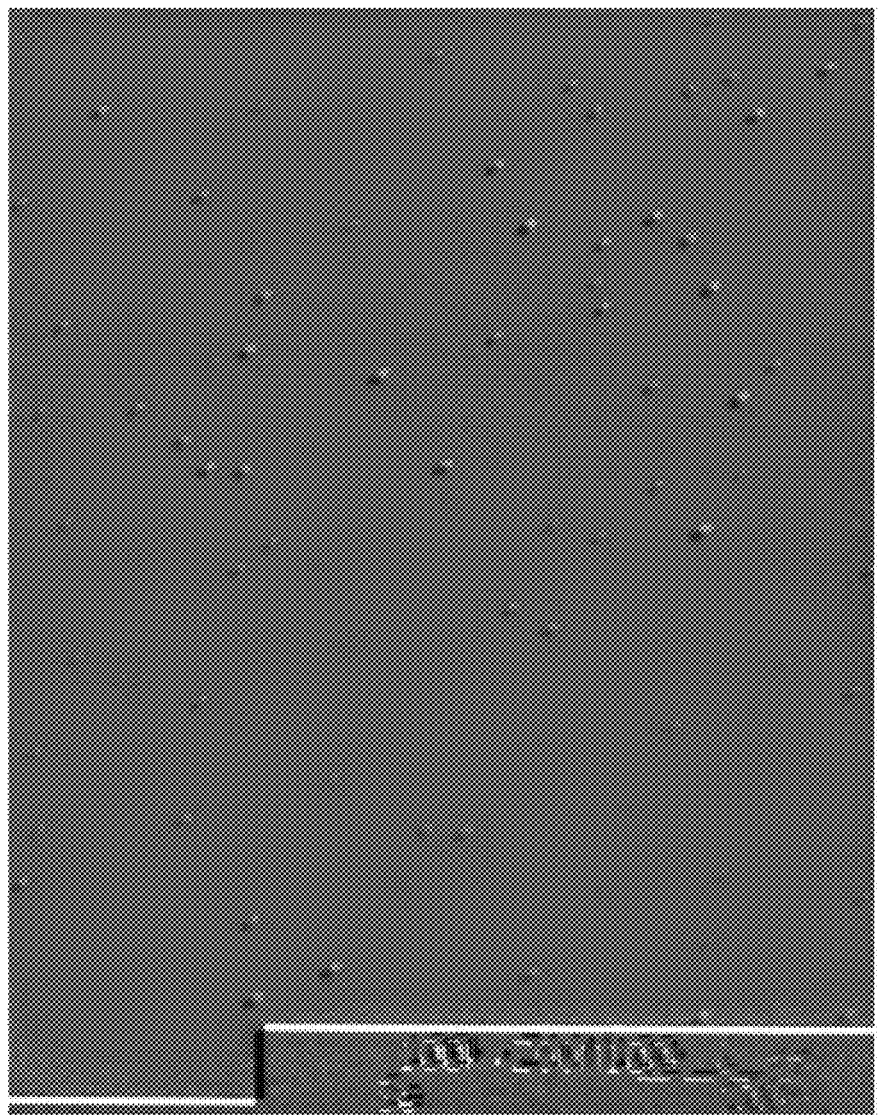
FIG. 5 is a transmission electron microscope (TEM) photograph of nano organic selenium particles.

FIG. 5 is a transmission electron microscope (TEM) photograph of nano organic selenium particles.

The organic selenium used in the present invention has a purity of 99.9% and a particle size of 1-20 nm, and is mixed in an amount of 0.1-10 ppm in the soap raw material. Organic selenium has anti-fungal and anti-oxidative effects.

In particular, organic selenium is known to have anti-oxidation action, which prevents aging, 2,000 times the vitamin C, by generating an enzyme called glutathione-peroxidase to protect cells from active oxygen, that is, active oxygen superoxide.

The functional soap of the present invention includes nanoscale platinum, gold, silver, organic germanium and organic selenium, so that it has anti-bacterial, sterilization, skin irritation relieving and skin moisturizing functions which are provided in the platinum, gold, silver, organic germanium and organic selenium, in addition to the washing effect of the conventional soap.

A mixing ratio of the functional soap according to examples of the present invention is shown in Table 1 below.

Example 1

TABLE 1

| Ingredient | | Content Rate (%) |
|---|---|---|
| 1. Soap Base | | 92.2 |
| 2. Water | | 2.0 |
| 3. *Simmondsia chinensis* (Jojoba) Seed Oil | | 0.4 |
| 4. Aloe Barbadensis Leaf Extract | | 0.3 |
| 5. *Eriocephalus punctulatus* Oil | | 0.4 |
| 6. Tocopherol | | 0.3 |
| 7. Phytosqualane | | 0.4 |
| 8. *Vitis vinifera* (Grape)seed Oil | | 0.5 |
| 9. *Melaleuca alternifolia* (Tea Tree) Leaf Oil | | 0.5 |
| 10. *Ampelopsis japonica* Root Extract | | 0.2 |
| 11. *Acorus gramineus* Root/stem Extract | | 0.2 |
| 12. *Prunus armeniaca* (Apricot) Kernel Extract | | 0.2 |
| 13. *Artemisia vulgaris* Extract | | 0.2 |
| 14. *Sophora angustifolia* Root Extract | | 0.2 |
| 15. Silkworm Extract | | 0.2 |
| 16. Ginkgo biloba Leaf Extract | | 0.2 |
| 17. *Mentha arvensis* Extract | | 0.2 |
| 18. *Phaseolus radiatus* Seed Extract *Vigna radiata* Seed Extract | | 0.2 |
| 19. Cnidium Officinale Root Extract | | 0.2 |
| 20. Perfume | | 1.0 |
| No. 2 Water contains | Silver | 0.0007 |
| | Germanium | 0.0005 |
| | Selenium | 0.0005 |
| | Platinum | 0.00005 |
| | Gold | 0.00005 |
| | Witch Hazel | 0.001 |
| TOTAL | | 100 |

Characteristics of the ingredients shown in Table as follows.

The main raw material of a soap base includes Coconut ingredient, and ingredients such as jojoba Seed Oil, Aloe Barbadensis Leaf Extract, Chamomile Oil, Tocopherol, Phytosqualane, and Grape Seed Oil etc., are mixed with nanoparticles of platinum, gold, silver, organic germanium and organic selenium to prepare a hard soap by way of a soap preparing process.

Example 2

Antibiotic tests were conducted on the functional soap using methicillin resistance staphylococus aureus (MRSA, ATCC 33592) as a used test strain. Results were obtained one minute after applying a 'KS M 0146' test method of germicidal power test. As a specimen, soap was diluted 100 times to concentration 1%. The bacteriostatic reduction ratio (%) was obtained from '(Ma−Mc)/Mb]×100', and an increase ratio (F) is 'Mb/Ma', wherein Ma is the number of viable cells counted immediately after inoculation of control sample. The colony forming unit concentration (CFU/ml) was $1.3 \times 10^5$, Ma $1.3 \times 10^5$, Mb $1.4 \times 10^5$, Mc<10, and the bacteriostatic reduction ratio was 99.9%, which is the germicidal power obtained.

It can be seen from the above test results that the soap according to the present invention mixed with nanoparticles having antibiotic functions shown an excellent antibiotic activity.

While the present invention has been described with reference to the preferred embodiments, it will be understood by those skilled in the related art that various modifications and variations may be made therein without departing from the scope of the present invention as defined by the appended claims.

What is claimed is:

1. A soap which contains a raw material of a soap base, and nanoscale platinum, gold, silver, organic germanium and organic selenium mixed in the raw material, in which the platinum has a purity of 99.9% and a particle size of 1-50 nm, and is mixed in an amount of 0.2-10 ppm, the gold has a purity of 99.9%, a particle size of 1-9 nm, and is mixed in an amount of 0.5-20 ppm, the silver has a purity of 99.9%, a particle size of 1-9 nm, and is mixed in an amount of 0.5-20 ppm, the organic germanium has a purity of 99.9%, a particle size of 5-50 nm, and is mixed in an amount of 0.1-10 ppm, and the organic selenium has a purity of 99.9%, a particle size of 1-20 nm, and is mixed in an amount of 0.1-10 ppm, wherein the raw material comprises coconut kernel and oil ingredient as main ingredients, the platinum, gold, silver, organic germanium and organic selenium are mixed in a main raw material of soap base in nanoparticles, and the nanoparticles mixed in the raw material comprise Jojoba Seed Oil, Aloe Barbadensis Leaf Extract, Chamomile Oil, Tocopherol, Phytosqualane and Grape Seed Oil ingredients which are mixed therein as supplemental agents.

\* \* \* \* \*